United States Patent [19]

Bukamier et al.

[11] Patent Number: 4,620,918

[45] Date of Patent: Nov. 4, 1986

[54] SELECTIVE SENSOR CONSTRUCTION

[76] Inventors: Gary L. Bukamier, 4341 Eureka; Steven L. Rupert, 5616 Whitewater St., both of Yorba Linda, Calif. 92686

[21] Appl. No.: 730,097

[22] Filed: May 3, 1985

[51] Int. Cl.[4] .............................................. G01N 27/30

[52] U.S. Cl. .................................... 204/403; 128/635; 204/415

[58] Field of Search ............... 204/415, 414, 403, 416, 204/418, 419, 420; 128/635

[56] References Cited

U.S. PATENT DOCUMENTS

| | | | |
|---|---|---|---|
| 3,259,124 | 7/1966 | Hillier | 204/415 X |
| 3,758,398 | 9/1973 | Doniguian | 204/415 |
| 3,835,013 | 9/1974 | Grubb et al. | 204/415 |
| 3,875,037 | 4/1975 | Krull | 204/415 |
| 3,887,194 | 6/1975 | Porter et al. | 204/415 X |
| 3,957,613 | 5/1976 | Macur | 204/415 X |
| 4,400,258 | 8/1983 | Han-Jürgen et al. | 204/415 |
| 4,441,979 | 4/1984 | Dailey | 204/402 |
| 4,444,646 | 4/1984 | Metzger et al. | 204/415 |
| 4,479,865 | 10/1984 | Beder et al. | 204/415 |

OTHER PUBLICATIONS

P. J. Radlett et al., Lab. Pract., vol. 21, No. 11, pp. 811, 812 & 814, (Nov. 1972).

*Primary Examiner*—G. L. Kaplan

*Attorney, Agent, or Firm*—Grover A. Frater

[57] ABSTRACT

A sterilizable electrode employs a selectively permeable membrane bonded at its edges to a face of a cover member. An opening or hole in the cover permits contact between the membrane and a material whose composition is to be tested. The cover and membrane assembly are removably attached to an electrolyte filled sensor body which also houses an electrode. The electrode is arranged to bear against the membrane to force the latter to bulge into the hole of the cover. In a dissolved oxygen sensor embodiment the electrode is a body of silver connected to a silver wire which extends through an inert, insulating sheath. The sheath is contained within a stainless steel shield which serves as the electrical conductor to, and a supporting structure for, a lead anode.

11 Claims, 7 Drawing Figures

38 50 52 12 60 66 58 24 70 62 72 78 56 76 48 54 30 82 80 68

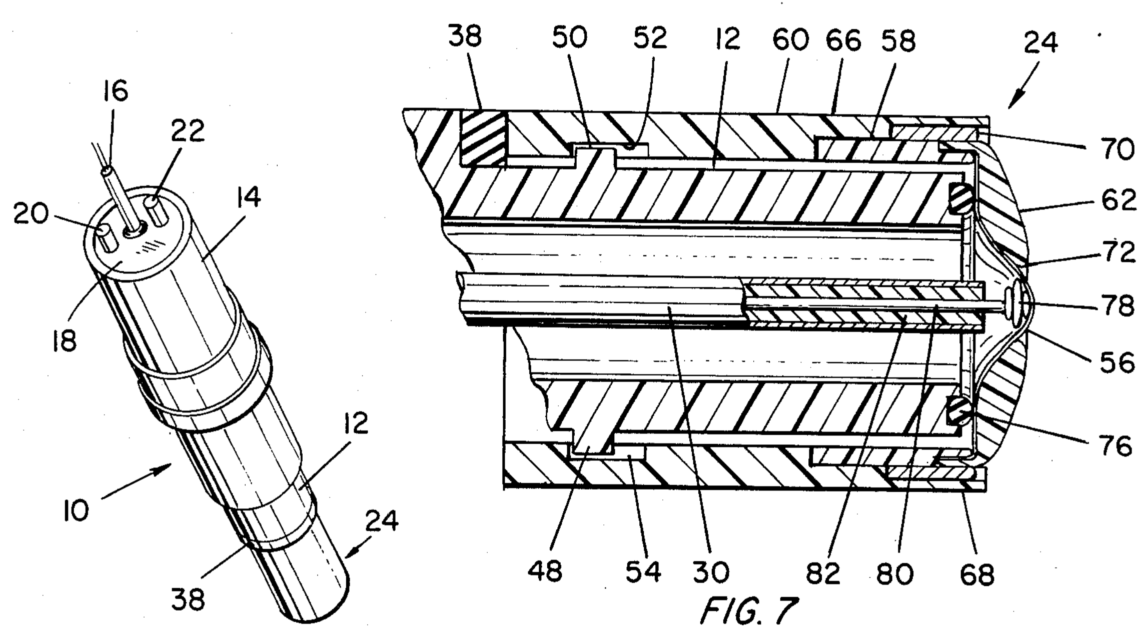
FIG. 1
FIG. 7
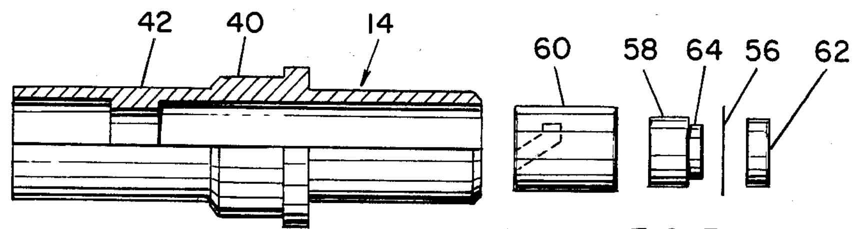
FIG. 3
FIG. 5
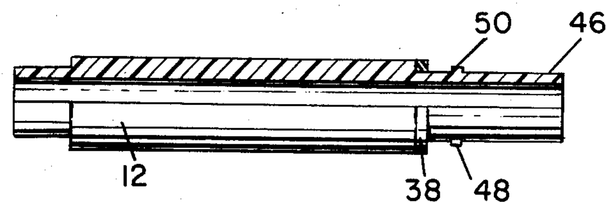
FIG. 4
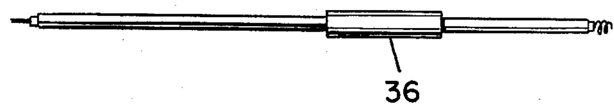
FIG. 6
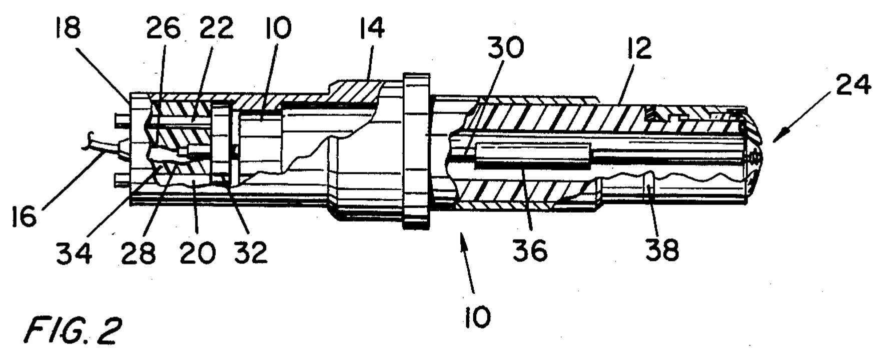
FIG. 2

SELECTIVE SENSOR CONSTRUCTION

TECHNICAL FIELD

This invention relates in general to improvements in selective sensors of the kind which utilize selectively permeable membranes, and it relates in particular to sensor constructions which can withstand sterilization at elevated temperature and pressure.

BACKGROUND ART

Electro-chemists live with the reality that electro-chemical signal levels are very low and that such signals are found everywhere. Moreover, while the chemical materials differ, the signals do not. They are all electrical, to be measured as a current or a voltage, and they are to be distinguished from other electro-chemical signals and from electrical noise the amplitude of which can approach or exceed the electro-chemical signal levels. It is in such an environment that designers of chemically selective electrodes do their work. In a common electrode form a galvanic cell is created by immersing two dissimilar metal electrodes in an electrolyte which is rendered effective by the introduction of ions or molecules of a given kind. The substance to be detected is introduced by permeation through a selectively permeable membrane. In another common form a polarizing unit or galvanic cell is formed by two half cells. The two electrodes are placed in contact with electrolyte in separate containing structures and the electrolyte path is completed through a selective membrane and a fluid which is to be tested for presence and concentration of the selected ion.

The chemical and electrical design of such electrodes must be complemented by a structural design which minimizes the possibility of the introduction in the electrical path of interfering ions (poisoning of the electrolyte) or corrosion of the metallic elements of the path. In addition, the structural design must take into account the environment and the character of the process in which the electrode will be used. The structure used in in vivo measurement of blood chemistry and the structures used to detect pollutants in exhaust gasses and the composition in fermentation vats may be very different from one another. While electro-chemical designs are often useful in a wide variety of applications, the task of creating complementary designs which are practical in a given application goes on. Cost, manufacturing and installation and servicing cost, is an especially important consideration in making electro-chemical measurement feasible in an ever widening range of applications. One of the needs of the sensor industry has been to find an improved structural design for sterilizable, membrane type sensors, and it is to that problem that this invention relates.

SUMMARY OF THE INVENTION

It is an object of the invention to provide an improved electro-chemical sensor construction.

Other objects are to provide a membrane arrangement capable of withstanding repeated sterilizations, which can be manufactured and serviced at minimum cost in accurate, reproducible and reliable form.

One particular purpose is to provide an improved dissolved oxygen sensor, especially one for use in monitoring the progress of a wide variety of processes including, but not limited to, fermentation and waste water monitoring and control.

These and other objects and advantages of the invention which will become apparent upon an examination of the accompanying drawings and the following specification are realized in part by the incorporation of an ion selective membrane in an assembly in which it lies against a relatively large surface where it is held by a body of electrolyte and such that a relatively small area of its opposite surface is exposed to the material to be tested. In preferred form the membrane is elastic and is stretched in the direction of the test material by one of the sensor's electrodes. One feature is that the membrane is made an integral part of a relatively low cost, replaceable assembly which permits reconstruction or refurbishing sensors to properly operating form conveniently and inexpensively. It is another feature that the replaceable assembly is attached to the main body of the structure with a twisting motion such as occurs when completing a bayonet fastener connection so that the electrode wipes against the membrane to insure separation by only a thin film of electrolyte.

In the single cell form of the invention the electrodes are held positioned and are electrically insulated from one another by a tube of chemically inert metal which is lined with a sheath or tube of inert plastic. A body of one electrode material, ordinarily the anode, is fixed to the metal tube mechanically and electrically. The other electrode, ordinarily the cathode, is mounted clear of the metal tube on a conductor which is made of the same material as is said other electrode. That conductor extends through the metal tube to a point outside of the electrolyte where both the metal tube and the conductor are connected to an external circuit.

BRIEF DESCRIPTION OF THE DRAWINGS

In the drawings:

FIG. 1 is an isometric view of a preferred sensor in which the invention is embodied;

FIG. 2 is a partially sectioned, side elevational view of the sensor;

FIG. 3 is a partly sectioned view of the outer body of the sensor;

FIG. 4 is a partly sectioned view of the inner body of the sensor;

FIG. 5 is an exploded view of the removable membrane assembly of the sensor;

FIG. 6 is an elevational view of the electrode assembly; and

FIG. 7 is an enlarged cross-sectional view of the forward end of the sensor.

DESCRIPTION OF THE PREFERRED EMBODIMENT

The sensor 10 of FIG. 1 includes electrodes and an electrolyte designed for the measurement of dissolved oxygen. Except for that, the structural arrangement is applicable to measurement or detection of a number of different ions and molecules, and it can house either a whole or half galvanic or polarizing cell in which selectivity is accomplished with an ion selective membrane.

The electrolyte and the electrodes are contained in an inner housing 12. An outer housing 14, into which one end of the inner housing is telescoped, serves to house the electrical connections between the electrodes and the shielded cable 16 of the external circuitry and the "plug" of epoxy material by which the electrolyte is precluded from leaking from the rearward or outer end 18 of the unit. The two short tubes 20 and 22 which protrude from that outer end permit filling the unit with electrolyte using a syringe and venting all air. They are sealed with a self sealing silastic rubber. The outer housing also includes the surfaces by which the unit is mounted in a fermentation vessel.

The inner end 24 is removable. One of its functions is to seal the electrolyte in the inner housing; another is to hold the ion selective membrane which forms part of the inner end or membrane assembly.

The unit 10 of FIG. 1 is shown in side elevation in FIG. 2. Part of the outer housing is broken away to show the electrical connection 26 between the inner silver conductor and the coaxial cable 16 and the connection 28 between the cable 16 and the stainless steel tube 30. The fill tubes 20 and 22 terminate in plug 32. The remainder of the space between the plug 32 and outer end 18 of the housing is filled with an epoxy plug 34.

At the inner end of the unit, portions of the inner and outer housings and the membrane assembly are broken away to reveal the cylindrical lead anode 36, the stainless steel tube 30 which extends through the anode and to which the anode is fixed and electrically connected. The space within the inner housing is filled with electrolyte in the finished sensor but has been omitted from the drawing for the sake of clarity. The numeral 38 identifies a gasket whose purpose is to preclude the material to be tested from entering the space between the inner body and the removable membrane assembly. The arrangement of the gasket and the structure of the elements at the inner end of the sensor are shown enlarged in FIG. 7.

The shape of the outer body facilitates the task of mounting. The central region 40 of the outer surface is devoted to that purpose. On the inner surface, a section 42 having reduced diameter and best seen in FIG. 3, serves as a stop and a locator for the plug 32 and the outer end of the inner housing 12. In this model, the remainder of the outer housing has a smooth bore of uniform diameter. So, too, does the inner housing 12, most of which is best seen in FIG. 4. The housing wall was reduced outer diameter at its inner end. The shoulder formed by the change in diameter cooperates with section 42 of the outer body to limit the degree insertion and to locate the inner housing.

The outer diameter of the housing 12 has reduced diameter over a relatively long section 46 of the housing's inner end. The outer surface has uniform diameter over section 46 except for the inclusion or addition of threads or other fastening conformations by which the membrane assembly may be removably fastened to the housing. This preferred model utilizes a bayonet fastening system. The pins are fixed to the inner housing and are numbered 48 and 50, respectively. They cooperate with grooves formed on the inner surface of the membrane assembly to hold that assembly on the inner end of the inner housing. One of those grooves 52 is shown in dotted lines in FIG. 5. Both grooves 52 and 54 are visible in the sectioned view of FIG. 7.

In this preferred form of the invention all of the components are symmetrical about the central axis of the unit and that includes the electrode assembly of FIG. 6 and the membrane assembly 24 the four elements of which are shown exploded in FIG. 5. Those elements include the membrane 56, an inner sleeve 58, an outer sleeve 60 and an end cover or cap 62. The membrane is formed as a circle of thin sheet material which is impervious to all it might encounter except a selected ion. In this case, the unit is to sense dissolved oxygen so that membrane is made of one of several materials that is permeable by oxygen molecules. In this preferred form a polyfluoronated hydrocarbon polymer is employed which can be bonded by the application of heat to the glass filled thermoplastic such as the polyethersulfone of which the cover 62 and the inner sleeve are formed. The forward or inner end of the inner sleeve 58 has reduced diameter at 64 so that it is readily inserted into a recess in the outer or rear face of the cover 62 when the membrane is positioned to overlie the recess of the cover. The cover, membrane and inner sleeve are forced together so that the margins of the membrane are pinched between the outer wall of section 64 of the sleeve and the inner wall of the cover's recess. This sub-assembly is heated at its periphery to bond the margins of the membrane to both the cover and the inner sleeve a best shown in FIG. 7.

The inner surface of the forward end of the outer sleeve is stepped to increased diameter at a section 66 is stepped to even greater inside diameter at an adjacent section 68 at the end of the outer sleeve. The inside diameter at section 66 is the same as the outside diameter of the inner sleeve 58 and the latter is press-fitted into section 66 of the outer sleeve to seat at the end of the section. The end section 68 of the outer sleeve having greater inside diameter, a deep recess remains between section 68 and the outer cylindrical surface of the very end of sleeve 58 and of cover 56. That recess is filled with a body of adhesive 70 which completes the bond between the membrane sub-assembly and the outer sleeve. The membrane is fixed to the cover and inner sleeve only at its margins. The entire central region overlies the rearward face of the cover except that the cover is formed with a relatively small, axial hole. The cover in this model has both its front and rear surface tapered outwardly or forwardly toward its central region. The cover is relatively thin at the margin of the hole and that margin 72 is rounded, particularly at the cover's rear surface, so that the central region of the membrane may be stretched into, and even through, the hole as portion 72 of the membrane is shown to be in FIG. 7 without injury to the membrane.

In the completely assembled unit the central region of the elastic membrane is forced to protrude through the cover hole by the cathode 78 of the electrode assembly. Because the membrane is not fixed to the cover except at its margins, stretching is not confined to the portion of the membrane which overlies the cover hole and the membrane is readily forced through the hole where it can make intimate contact with the material whose dissolved oxygen content is to be measured.

The membrane assembly is formed of relatively inexpensive materials and can be manufactured at low cost with a high degree of dimensional uniformity. Accordingly, it can be treated as a disposable element. In the usual case it is the electrolyte that fails first. Sensor bodies made according to the invention can be dissembled to remove the electrolyte by mere removal of the membrane assembly. In this case removal is accomplished by twisting the membrane assembly relative to the remainder of the unit to unlock the bayonet fastening elements and sliding the assembly from the inner housing. While the membrane assembly could be reused, the replacement cost is so low that an attempt to reuse the old assembly is usually unwarranted. Unlike prior art designs, replacement does not involve the need to position and secure the membrane itself. With this design all assembly and securing of the membrane in the cover is accomplished in a factory assembly and test environment.

The bayonet fastening system serves as more than a convenience to assembly. It requires a forcing and a limited twisting motion which insures some conformance of the membrane to cathode shape and intimate contact of cathode and membrane with only a film of electrolyte between them. Uniform performance of electrodes thus assembled is achieved notwithstanding minor dimensional differences in cathodes. The amount of twisting required by a threaded connection would preclude use of a very thin membrane but the limited turning in the bayonet connection does not.

Fresh electrolyte is introduced at the fill tubes and is sealed in the inner housing at the rear by the plugs 32 and 34 and at the forward end by an O-ring 76 which is mounted in an annular recess in the front rim of the inner housing. That O-ring is pressed against the inner side of the membrane 56 and is held compressed by the bayonet fastening elements which lock membrane assembly and inner housing together. The annular elastic seal 38 is compressed between the assembly 24 and inner housing 12 in the locking process. The seal, which in this design is square in cross-section when relaxed, serves to preclude the material being tested or measured from entering the space between assembly 24 and the inner housing. The bayonet lock can be replaced by screw threads or other fastening arrangements, but the bayonet connection is preferred. It involves a small degree of twisting of the O-ring against the membrane to insure sealing but not enough to twist and distort the membrane.

In this unit the electrolyte must be one that will not vaporize during steam sterilization. The preferred electrolyte used here comprises sodium hydroxide, propionic acid and glycerol and has a boiling point no lower than 135 degrees Celsius. The electrodes are formed of lead in the case of anode 36 (FIGS. 2 and 6) and silver in the case of cathode 78 (FIG. 7). The conductor 80 by which the cathode is connected to coaxial cable 16 is a silver wire. In this preferred form any possibility of a junction potential being developed at the junction of the conductor and the cathode is eliminated by forming the cathode as several twists at the end of the silver wire. The wire is twisted to form a structure, the cathode, which is smaller in diameter than the central opening of cover 62 and can force the membrane to bulge through the hole. The wire is threaded through the central opening of a plastic sheath 82 and the sheath is telescoped and disposed within the stainless steel tube 30. The inside diameter of the sheath is only slightly larger or is the same as the diameter of the silver wire and the outer diameter of the sheath approaches the inner diameter of the stainless steel tube. The silver conductor wire protrudes only a short distance from the sheath and tube at each end. Thus, the tube and sheath serve as a mechanical support for the conductor wire. And the cathode being fitted into the hole of the cover and held centered there by the membrane, serves to confine the electrode assembly to the axis of the unit. The other end of the electrode assembly is held on the axis of the unit by the plug 32 through which it extends as best shown in FIG. 2. The stainless steel tube is inert in this electrolyte as is the plastic sheath, and it also serves as a shield for the silver conductor against magnetic and electric fields.

The silver electrode, being formed of twists or coils of wire, has interstices into which electrolyte may flow and from which, by surface tension, the surface of the electrode is wetted by a thin layer of electrolyte. That layer extends between the electrode and the membrane. The membrane is free to flow inwardly in its area around the cathode 78 and to bulge outwardly in even greater degree to accommodate pressure change and electrolyte volumetric change during sterilization cycles. The result is an electrode which can withstand many sterilization cycles and which can be constructed and serviced at substantially less cost than prior art devices in many applications.

In obedience to the rules, the best mode now known for practicing the invention has been shown in the accompanying drawing and described in the specification above. However, it is to be understood that other embodiments and variations of the invention are possible and that the invention is to be limited by what is defined in the appended claims rather than by what has been shown.

We claim:

1. For inclusion in a chemically selective sensor of the kind in which two spaced electrodes are bridged by an electrolyte and separated from the external environment by a membrane which is permeable by selected ions or molecules, in combination:

an electrode and electrolyte container having a wall formed with an opening of given size;

a membrane disposed to cover said opening, the membrane being fixed to said container at the margins of said opening entirely around said opening;

a cover formed with a through hole and fixed to the container overlying the membrane such that said hole overlies a central region of said membrane;

said container comprising a generally cylindrical tube one open end of which forms said opening;

said cover forming a closure for said one open end; and said container comprising a second tube telescoped into the first mentioned tube such that an open end of said second tube is sealed against said membrane.

2. The invention defined in claim 1 which further comprises an electrode disposed within said second tube such that it bears against said membrane at the side of said membrane away from said cover at a point opposite said hole of the cover.

3. The invention defined in claim 2 which further comprises a bayonet connection between said first mentioned tube and said second tube.

4. The invention defined in claim 2 which further comprises a body of electrolyte disposed in said second tube; and means for releasably interconnecting said tubes such that the body of electrolyte is confined to said second tube by sealing engagement of said second tube with said membrane.

5. The invention defined in claim 4 in which said end of said second tube comprises an O-ring and sealing of said second tube against said membrane is accomplished by said O-ring.

6. The invention defined in claim 2 in which said membrane is resilient and in which said electrode is effective to stretch said membrane through said hole formed in said cover.

7. The invention defined in claim 2 which further comprises a bayonet connection between said first mentioned tube and said second tube.

8. The invention defined in claim 2 in which further comprises:

a metallic tube;

a second electrode fixed to said metallic tube;

a tubular, electrically insulating sheath telescoped within said metallic tube; and an electrical conductor extending through said sheath;

said electrode first mentioned being fixed to said electrical conductor.

9. The invention defined in claim 8 in which said first mentioned electrode and said electrical conductor are formed of silver, said metallic tube being formed of stainless steel and said second conductor being formed of lead.

10. The invention defined in claim 9 which further comprises a body of electrolyte disposed in said second tube; and means for releasably interconnecting said tubes such that the body of electrolyte is confined to said second tube by sealing engagement of said second tube with said membrane.

11. An electrode assembly for a chemically selective galvanic cell which is to incorporate an anode and a cathode and a body of a given acidic electrolyte material which is to contact said cathode and in which said anode is to be immersed, said assembly comprising:

an elongated, electrically insulated electric conductor electrically and mechanically connected at one end to said cathode;

a tube of electrically conductive stainless steel material which is chemically inert to said given electrolyte, the elongated insulated conductor extending through said tube; and a body of anode material comprising lead fixed to said tube at a point removed from said one end of said wire and from said cathode, the body of cathode material being electrically connected to said tube.

* * * * *